(12) United States Patent
Rana et al.

(10) Patent No.: US 9,801,809 B2
(45) Date of Patent: Oct. 31, 2017

(54) COMPOSITIONS INCLUDING A BOTANICAL EXTRACT AND METHODS OF USING THE SAME IN SKIN WHITENING AND SKIN LIGHTENING APPLICATIONS

(71) Applicant: Access Business Group International LLC, Ada, MI (US)

(72) Inventors: Jatinder Rana, Grand Rapids, MI (US); Ganesh Diwakar, Irvine, CA (US); XiaoJuan Shen, Shanghai (CN); Jeffrey Scholten, Grand Rapids, MI (US); Rebecca Miller, Lowell, MI (US)

(73) Assignee: Access Business Group International LLC, Ada, MI (US)

( * ) Notice: Subject to any disclaimer, the term of this patent is extended or adjusted under 35 U.S.C. 154(b) by 263 days.

(21) Appl. No.: 14/703,408

(22) Filed: May 4, 2015

(65) Prior Publication Data
US 2015/0313835 A1 Nov. 5, 2015

Related U.S. Application Data

(60) Provisional application No. 61/988,576, filed on May 5, 2014, provisional application No. 62/103,202, filed on Jan. 14, 2015.

(51) Int. Cl.
| | |
|---|---|
| *A61K 36/00* | (2006.01) |
| *A61K 8/97* | (2017.01) |
| *A61K 8/60* | (2006.01) |
| *A61Q 19/02* | (2006.01) |
| *A61K 36/185* | (2006.01) |
| *A61K 36/23* | (2006.01) |
| *A61K 36/28* | (2006.01) |
| *A61K 36/286* | (2006.01) |
| *A61K 36/287* | (2006.01) |
| *A61K 36/288* | (2006.01) |
| *A61K 36/48* | (2006.01) |
| *A61K 36/481* | (2006.01) |
| *A61K 36/489* | (2006.01) |

(52) U.S. Cl.
CPC ............ *A61K 8/97* (2013.01); *A61K 8/602* (2013.01); *A61K 36/185* (2013.01); *A61K 36/23* (2013.01); *A61K 36/28* (2013.01); *A61K 36/286* (2013.01); *A61K 36/287* (2013.01); *A61K 36/288* (2013.01); *A61K 36/48* (2013.01); *A61K 36/481* (2013.01); *A61K 36/489* (2013.01); *A61Q 19/02* (2013.01); *A61K 2800/70* (2013.01); *A61K 2800/782* (2013.01)

(58) Field of Classification Search
None
See application file for complete search history.

(56) References Cited

FOREIGN PATENT DOCUMENTS

| | | | |
|---|---|---|---|
| CN | 102302542 A | * | 1/2012 |
| CN | 102415979 A | * | 4/2012 |
| JP | 2003 201208 A | | 7/2003 |
| JP | 2011 105644 A | | 6/2011 |
| JP | 2011 246353 A | | 12/2011 |
| KR | 2006108864 A | * | 10/2006 |
| WO | WO 2015/171475 | | 11/2015 |

OTHER PUBLICATIONS

Sun et al, Flavonoids and volatiles in Chrysanthemum morifolium Ramat flower from Tongxiang County in China. African Journal of Biotechnology (2010), vol. 9. No. 25, pp. 3817-3821.*
International Search Report issued in the corresponding International Application No. PCT/US2015/028990, dated Oct. 28, 2015.
Written Opinion of the International Searching Authority issued in the corresponding International Application No. PCT/US2015/028990, dated Oct. 28, 2015.
Murga et al., "Extraction of Natural Complex Phenols and Tannins from Grape Seeds by Using Supercritical Mixtures of Carbon Dioxide and Alcohol." *J. Agric Food Chem.*, 48:3408-3412 (2000).
Hong et al., "Microwave-Assisted Extraction of Phenolic Compounds From Grape Seed." *Nat Prod Lett.*, 15(3):197-204 (2001).
Ashraf-Khorassani et al., "Sequential Fractionation of Grape Seeds into Oils, Polyphenols, and Procyanidins via a Single System Employing $CO_2$-Based Fluids," *J. Agric Food Chem.*, 52:2440-2444 (2004).
Remington's Pharmaceutical Sciences, Gennaro, Mack Publishing Co., Easton Pa., 1990.
Ni-Komatsu et al., "Triazine-based tyrosinase inhibitors identified by chemical genetic screening," *Pigment Cell Res.*, 18:447-453 (2005).
Rana, et al., "Inhibition of melanin content by *Punicalagins* in the super fruit pomegranate (*Punica granatum*)," *J. Cosmet. Sci.*, 64:445-453 (2013).
Kim and Uyama, "Tyrosinase inhibitors from natural and synthetic sources: structure, inhibition mechanism and perspective for the future," *CMLS, Cell. Mol. Life Sci.*, 62:1707-1723 (2005).
Mintel Database, "Mineral Cleansing Mask," *African Botanics*, Record ID No. 2358788 (2014).
Mintel Database, "Anti-Aging Blemish Control Spot Treatment," *June Jacobs*, Record ID No. 1960149 (2013).
Communication Relating to the Results of the Partial International Search received in PCT Application No. PCT/US2015/028990, dated Jul. 22, 2015.

* cited by examiner

*Primary Examiner* — Qiuwen Mi
(74) *Attorney, Agent, or Firm* — Brinks Gilson & Lione (57) ABSTRACT

Compositions for topical use and having a melanin synthesis-inhibiting activity that include an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium* effective to reduce melanin synthesis are described. Methods for inhibiting melanin synthesis and for skin whitening are also described.

9 Claims, 3 Drawing Sheets

Figure 1

HPLC Fingerprint Profile of Chrysanthemum: Identification of L7G as an "Active" Marker for Skin Lightening Activity

Figure 2

ICR Application: Skin Lightening Activity of Chrysanthemum morifolium Extract

Dose Dependent Inhibition of Tyrosine Enzyme Activity by Chrysanthemum Extract

Figure 3

COMPOSITIONS INCLUDING A BOTANICAL EXTRACT AND METHODS OF USING THE SAME IN SKIN WHITENING AND SKIN LIGHTENING APPLICATIONS

RELATED APPLICATIONS

The present patent document claims the benefit of the filing date under 35 U.S.C. §119(e) of Provisional U.S. Patent Application Ser. Nos. 61/988,576, filed May 5, 2014 and 62/103,202, filed Jan. 14, 2015, which are hereby incorporated by reference.

BACKGROUND

Compositions that include a botanical extract and their use in the methods of skin whitening or lightening as well as methods of inhibiting melanin synthesis in the skin are described.

Skin color is primarily determined by the amount of melanin in the skin. Melanin is a brown-black pigment present in the skin. Due to the dark color of the pigment, lower amounts of melanin result in lighter skin color while higher amounts result in darker skin color. Melanin is formed by the oxidation of the amino acid tyrosine to dihydroxyphenalanine in melanocytes. This reaction is catalyzed by the enzyme tyrosinase.

Excessive skin pigmentation may be caused by hormone abnormality in the human body, genetic diseases, etc., regardless of UV, or by excessive melanogenesis and melanin maldistribution due to excessive UV irradiation. A suitable amount of melanin in the skin has the positive effect of maintaining the skin healthy and absorbing UV, etc. However, excessive melanin results in negative effects, such as skin darkening and non-uniform skin color. Thus, many scientists have studied melanogenesis inhibition.

As a result of this pivotal role of tyrosinase in melanin formation, efforts to develop effective skin whitening compositions have focused on agents that inhibit the function and activity of tyrosinase. For example, compositions have been proposed that include a variety of known tyrosinase inhibitors, such as hydroquinone, vitamin C and its derivatives, kojic acid, arbutin, glutathione, cysteine, and mulberry extract, among others.

A problem with synthetic skin lighteners such as hydroquinone or kojic acid is that they may cause skin irritation or acute dermatitis. Thus, there is a continuing desire to incorporate natural sources into compositions in an attempt to address some of the undesirable aspects of synthetic products.

SUMMARY

One embodiment relates to a composition having a melanin synthesis-inhibiting activity, comprising an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* and *Chrysanthemum morifolium,* the botanical extract effective to reduce melanin synthesis. The botanical extract may be standardized with respect to luteolin-7 glucoside content. In some embodiments, it is standardized to about 0.5-50% luteolin-7 glucoside; alternatively, about 0.5-5%; alternatively, about 1-30%, or about 1.0% luteolin-7 glucoside. The botanical extract includes at least one of Yarrow Extract (*Achillea millefolium*), *Aspalathus Linearis* Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*). The composition may have a substantially neutral pH. The composition may be formulated for a topical or oral administration. In case of topical administration, the composition may be a preparation selected from the group consisting of cream, ointment, foam, lotion, plaster, tablets, granules, and emulsion. In case of topical preparation, the composition may further comprise one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes. The amount effective to reduce melanin synthesis may be from about 10 mg to about 1000 mg. In case of oral administration, the composition may be a preparation selected from the group consisting of a capsule, a tablet, a chewable tablet, a caplet, a lozenge, a dragée, a plurality of particles, granules, beads, powders, pellets, a liquid, a gel, a syrup, a slurry, a suspension, a nutritional bar, a soft gel, a semi-solid taffy-like chew, and a chewing gum. The composition may further comprise a skin whitening agent selected from the group consisting of tyrosinase inhibitors, free radical scavengers, and mixtures thereof. The ratio of the botanical extract to the skin whitening agent may be from about 100:1 to about 1:100. The botanical extract may form approximately 1-99% w/w of the composition. The botanical extract may form approximately 1-75% w/w of the composition. The botanical extract may form approximately 50-70% w/w of the composition. The botanical extract may be an aqueous extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium.* The composition may be for use in treating or preventing cholasma.

A further embodiment relates to a topical composition comprising a cosmetically acceptable vehicle and an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* and *Chrysanthemum morifolium* standardized to about 1.0% luteolin-7 glucoside, wherein the botanical extract forms approximately 1-99% w/w of the composition. The botanical extract may be Yarrow Extract (*Achillea millefolium*), *Aspalathus Linearis* Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), Chrysanthemum Extract (*Chrysanthemum morifolium*), or a combination thereof.

Yet further embodiment relates to an oral composition comprising a pharmaceutically acceptable vehicle and an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* and *Chrysanthemum morifolium* standardized to about 1.0% luteolin-7 glucoside, wherein the botanical extract forms approximately 1-99% w/w of the composition. The botanical extract may be Yarrow Extract (*Achillea millefolium*), *Aspalathus Linearis*

Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

Another embodiment relates to a method of whitening skin comprising topically applying to the skin a composition comprising an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium*, wherein the composition is applied in an amount and for a period of time sufficient to visibly whiten the skin. The botanical extract is standardized to about 0.5-50% luteolin-7 glucoside. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

A further embodiment relates to a method of whitening skin comprising orally administering to a subject a composition comprising an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium*, wherein the composition is administered in an amount and for a period of time sufficient to visibly whiten the skin of the subject. The botanical extract is standardized to about 0.5-50% luteolin-7 glucoside. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

In a topical skin whitening cosmetic composition containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, another embodiment relates to the improvement comprising an effective amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* to whiten the skin. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

A further embodiment relates to a method of visibly whitening human skin comprising topically applying to the skin a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium*, standardized with respect to luteolin-7 glucoside in an amount and for a period of time sufficient to visibly whiten the skin. The botanical extract is standardized to about 0.5-50% luteolin-7 glucoside. The botanical extract may be incorporated into a cosmetic preparation selected from the group consisting of cream, ointment, foam, lotion, plaster, tablets, granules, and emulsion. The cosmetic preparation may further comprise a skin whitening agent selected from the group consisting of tyrosinase inhibitors, free radical scavengers, and mixtures thereof. The ratio of the botanical extract to the skin whitening agent may be from about 100:1 to about 1:100. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

A further embodiment relates to a method of visibly whitening human skin in a subject comprising orally administering to the subject a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized with respect to luteolin-7 glucoside in an amount sufficient to visibly whiten the skin. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), Chrysanthemum Extract (*Chrysanthemum morifolium*), or a combination thereof.

Yet further embodiment relates to a method for inhibiting melanin synthesis comprising topically applying to the skin a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to reduce melanin synthesis, wherein the composition is applied in an amount and for a period of time sufficient to inhibit melanin synthesis in the skin. The botanical extract may be Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow

*Sophora* Extract (*Sophora flavescentis*), *Chrysanthemum* Extract (*Chrysanthemum morifolium*), or a combination thereof.

Another embodiment relates to a method for inhibiting melanin synthesis comprising orally administering to a subject a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to reduce melanin synthesis, wherein the composition is administered in an amount and for a period of time sufficient to inhibit melanin synthesis in the skin. The botanical extract may be Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), *Chrysanthemum* Extract (*Chrysanthemum morifolium*), or a combination thereof.

Yet another embodiment relates to a method for treating or preventing cholasma comprising topically applying to the skin of a subject a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to treat or prevent cholasma, wherein the composition is applied in an amount and for a period of time sufficient to treat or prevent cholasma in the skin of the subject. The botanical extract may be Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), *Chrysanthemum* Extract (*Chrysanthemum morifolium*), or a combination thereof.

Yet further embodiment relates to a method for treating or preventing cholasma comprising orally administering to a subject a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to treat or prevent cholasma, wherein the composition is administered in an amount and for a period of time sufficient to treat or prevent cholasma in the skin of the subject. The botanical extract may be Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), *Chrysanthemum* Extract (*Chrysanthemum morifolium*), or a combination thereof.

DETAILED DESCRIPTION

It is to be understood that this invention is not limited to the particular compositions, methodology, or protocols described herein. Further, unless defined otherwise, all technical and scientific terms used herein have the same meaning as commonly understood to one of ordinary skill in the art to which this invention belongs. It is also to be understood that the terminology used herein is for the purpose of describing particular embodiments only, and is not intended to limit the scope of the present invention, which will be limited only by the claims.

The present invention is based on the surprising discovery that a botanical extract (e.g., Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*)) that is standardized to about 1.0% luteolin-7 glucoside (L7G) provides a dose dependent effect on melanin production. As shown, for example in FIG. 3, melanin production is increasingly reduced or inhibited with an increase in the dose of *chrysanthemum* extract.

Accordingly, compositions that include a botanical extract in sufficient amounts to achieve a reduction in melanin production and their use in the methods of skin whitening or lightening are described.

Definitions

The term "composition" refers to a product that treats, improves, promotes, increases, manages, controls, maintains, optimizes, modifies, reduces, inhibits, or prevents a particular condition associated with a natural state, biological process or disease or disorder. The term composition includes, but is not limited to, pharmaceutical (i.e., drug), over-the counter (OTC), cosmetic, food, food ingredient or dietary supplement compositions that include an effective amount of an extract, at least one component thereof, or a mixture thereof. Exemplary compositions include cream, cosmetic lotion, pack or powder, or as an emulsion, lotion, liniment foam, tablets, plasters, granules, or ointment.

As used herein, the term "extract" or "botanical extract" refers to a solid, viscid, or liquid substance or preparation that includes an active ingredient(s) of a substance of plant, such as *Aspalathus Linearis, Matricaria, Saxifraga, Astragalus, Taraxacum officinale/mongolicum, Ferula varia/foetida, Carthamus tinctorius, Sophora flavescentis*, and/or *Chrysanthemum morifolium* in a concentrated form. The term "extract" is intended to include not only a crude extract produced from *Aspalathus Linearis, Matricaria, Saxifraga, Astragalus, Taraxacum officinale/mongolicum, Ferula varia/foetida, Carthamus tinctorius, Sophora flavescentis*, or *Chrysanthemum morifolium* by use of a solvent selected from among water, lower alcohols of 1 to 4 carbon atoms, such as methanol, ethanol, butanol, etc., ethylene, acetone, hexane, ether, chloroform, ethylacetate, butylacetate, dichloromethane, N,N-dimethylformamide (DMF), dimethylsulfoxide (DMSO), 1,3-butylene glycol, propylene glycol and a combination thereof, but also a fraction of the crude extract in such a solvent. So long as it assures the extraction and preservation of the active ingredient(s), any extraction method may be employed. Examples of botanical extracts include Yarrow Extract (*Achillea millefolium*), *Aspalathus Linearis* Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*).

As used herein, the term "effective amount" or "therapeutically effective amount" of a composition, extract, extract mixture, component of the extract, and/or active agent or ingredient refers to an amount effective at dosages and for periods of time sufficient to achieve a desired result. For example, the "effective amount" or "therapeutically effective amount" refers to that amount of a composition, extract, extract, extract mixture, botanical extract mixture, component of the extract, and/or active agent or ingredient of this invention which, when administered to a subject (e.g., mammal, such as a human), is sufficient to effect treatment, such as inhibiting melanin synthesis (i.e., melanogenesis), inhibiting expression and/or activity of tyrosinase enzyme, mitigating or preventing cholasma (i.e., a disorder of hyperpigmentation), skin whitening and/or lightening, decreasing or lightening dark spots and the like in a subject. The amount of a composition, extract, botanical extract, extract mixture, botanical extract mixture, component of the extract, and/or active agent or ingredient of this disclosure that constitutes an "effective amount" or "therapeutically effective treatment" will vary depending on the active agent or the compound, the condition being treated and its severity, the manner of administration, the duration of treatment, or the age of the subject to be treated, but can be determined routinely by one of ordinary skill in the art having regard to his own knowledge and to this disclosure.

The term "pharmaceutically acceptable" means those drugs, medicaments, extracts or inert ingredients, which are suitable for use in contact with the tissues of humans and lower animals without undue toxicity, incompatibility, instability, irritation, and the like, commensurate with a reasonable benefit/risk ratio.

The terms "administer," "administered," "administers" and "administering" are defined as providing a composition to a subject via a route known in the art, including but not limited to intravenous, intraarterial, oral, parenteral, buccal, topical, transdermal, rectal, intramuscular, subcutaneous, intraosseous, transmucosal, or intraperitoneal routes of administration. In preferred embodiments, topical routes of administering a composition are suitable.

As used herein, the term "subject" or "individual" includes mammals to which a composition may be administered. Non-limiting examples of mammals include humans, non-human primates, rodents (including transgenic and non-transgenic mice) or the like. In some embodiments, the subject is a mammal, and in some embodiments, the subject is human.

Botanical Sources of Luteolin-7 Glucoside

The botanical extract can include at least one of Yarrow Extract (*Achillea millefolium*), *Aspalathus Linearis* Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*), or a combination thereof.

Figure 3:
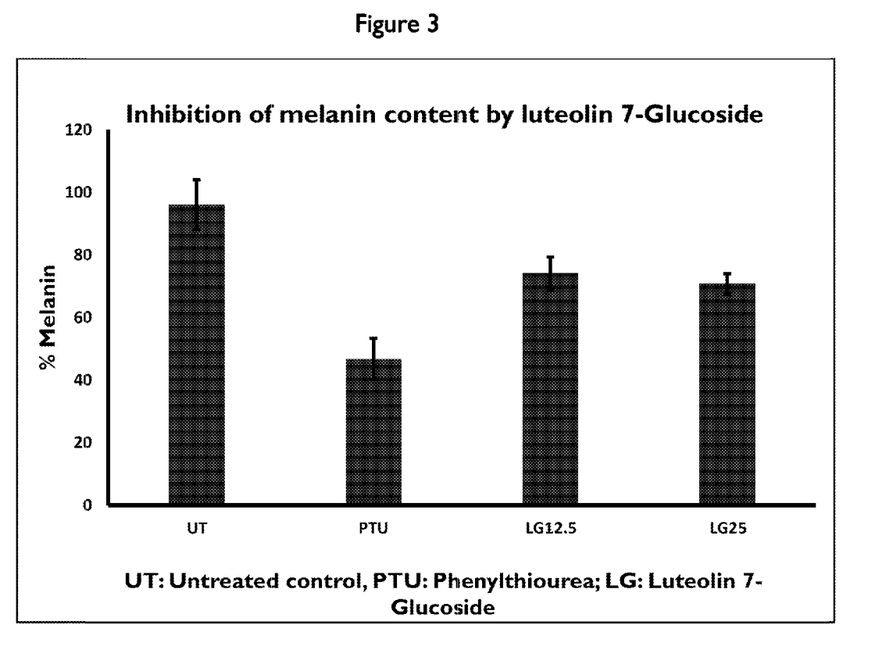
FIG. 3 depicts a graph showing dose-dependent inhibition of melanin content by luteolin-7 glucoside (L7G).

The extracts may be extracted with water to yield a botanical extract that is useful in unique compositions of the present invention. In certain aspects, the flower or capitulum of the plant is used as the source of the extract. When extracted, the botanical extract is standardized to luteolin-7 glucoside content. For example, the botanical extract may be standardized to about 1.0% luteolin-7 glucoside content. For example, the *chrysanthemum* extract that has been standardized to about 1.0% luteolin-7 glucoside provides a dose dependent reduction in melanin production (FIG. 3).

An exemplary structure of luteolin-7 glucoside ($C_{21}H_{20}O_{11}$) is shown below:

The botanical extracts of *Achillea millefolium, Aspalathus Linearis, Matricaria, Saxifraga, Astragalus, Taraxacum officinale/mongolicum, Ferula varia/foetida, Carthamus tinctorius, Sophora flavescentis*, or *Chrysanthemum morifolium* may be commercially obtained from various sources including Shanghai Novanat Co. In addition, a suitable botanical extract of *Achillea millefolium, Aspalathus Linearis, Matricaria, Saxifraga, Astragalus, Taraxacum officinale/mongolicum, Ferula varia/foetida, Carthamus tinctorius, Sophora flavescentis*, or *Chrysanthemum morifolium* may be obtained using any of the extraction techniques discussed more fully below or known in the art.

Exemplary Extraction Processes

In one example, a botanical extract useful in the unique compositions of the present invention might be obtained using an organic solvent extraction technique.

In another example, solvent sequential fractionation may be used to obtain a botanical extract useful in the unique compositions of the present invention.

Total hydro-ethanolic extraction techniques may also be used to obtain a botanical extract useful in the unique compositions of the present invention. Generally, this is referred to as a lump-sum extraction. The botanical extract generated in this process will contain a broad variety of phytochemicals present in the extracted material including fat and water solubles. Following collection of the botanical extract solution, the solvent will be evaporated, resulting in the botanical extract.

Total ethanol extraction may also be used in the present invention. This technique uses ethanol, rather than hydroethanol, as the solvent. This extraction technique generates an extract that may include fat soluble and/or lipophilic compounds in addition to water soluble compounds.

Another example of an extraction technique that may be used to obtain an extract useful in the present invention is supercritical fluid carbon dioxide extraction (SFE). In this extraction procedure the material to be extracted is not exposed to any organic solvents. Rather, the extraction solvent is carbon dioxide, with or without a modifier, in supercritical conditions (>31.3° C. and >73.8 bar). Those of skill in the art will appreciate that temperature and pressure conditions can be varied to obtain the best yield of extract. This technique generates an extract of fat soluble and/or lipophilic compounds, similar to the total hexane and ethyl acetate extraction technique described above.

Those of skill in the art will appreciate that there are many other extraction processes, both known in the art and described in various patents and publications that can be used to obtain the extracts to be used in practicing the present invention. For example, the extraction procedures described in the following references, which are incorporated herein by reference, could be used in practicing the present invention: Murga et al., "Extraction of natural complex phenols and tannins from grape seeds by using supercritical mixtures of carbon dioxide and alcohol." *J. Agric Food Chem.* 2000 August: 48(8):3408-12; Hong et al., "Microwave-assisted extraction of phenolic compounds from grape seed." *Nat Prod Lett.* 2001; 15(3):197-204; Ashraf-Khorassani et al., "Sequential fractionation of grape seeds into oils, polyphenols, and procyanidins via a single system employing $CO_2$-based fluids." *J. Agric Food Chem.*, 2004 May 5; 52(9):2440-4.

According to one example of the present invention, the botanical extract may be prepared by extracting a flower of a botanical with 100% water. For example, *chrysanthemum* extract may be prepared by extracting *Chrysanthemum Morifolium* flower with 100% water. Final extract has a moisture content of >5.0% to produce a plant extract with native extraction ratio of botanical:finished product 5-7:1. The *chrysanthemum* extract can then be assayed and standardized with respect to luteolin-7 glucoside content. In some embodiments, it is standardized to about 0.5-50% luteolin-7 glucoside; alternatively, about 1.0-30%; alternatively, about 0.5-5; or about 1.0% luteolin-7 glucoside. In certain preferred embodiments, the *chrysanthemum* extract is an aqueous extract of *chrysanthemum*, particularly the flower or capitulum of *chrysanthemum*.

Compositions

The botanical extract of *Achillea millefolium, Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium* may be formulated into a composition. Specifically, certain embodiments relate to a composition having a melanin synthesis-inhibiting activity that includes an amount of a botanical extract effective to reduce melanin synthesis. Certain other embodiments relate to a composition for skin whitening and/or skin lightening that includes an amount of a botanical extract effective to whiten or lighten the skin. Certain other embodiments relate to a composition for treating or preventing cholasma, a disorder of hyperpigmentation that includes an amount of a botanical extract effective to treat and/or prevent cholasma.

Compositions of the present invention may be formulated in an acceptable carrier or excipient and may be prepared, packaged, and labeled for cosmetic or pharmaceutical use in skin whitening or lightening, or treating or preventing cholasma in a subject.

The botanical extract forms approximately at least 50% w/w of the composition, more preferably, at least approximately 55% w/w composition, at least approximately 60% w/w composition, at least approximately 65% w/w composition, at least approximately 70% w/w composition, at least approximately 75% w/w composition, at least approximately 80% w/w composition, at least approximately 85% w/w composition, at least approximately 90% w/w composition, at least approximately 95% w/w composition, at least approximately 99% w/w composition. Alternatively, the botanical extract forms approximately 1-99% w/w of the composition; alternatively, the botanical extract forms approximately 1-90% w/w of the composition; alternatively, the botanical extract forms approximately 1-75% w/w of the composition; alternatively, the botanical extract forms approximately 50-70% w/w of the composition. Of course, one of skill in the art will appreciate that the amount of the extract incorporated into the composition may depend on the standardized content of luteolin-7 glucoside. Thus, if the botanical extract is standardized to about 40% luteolin-7 glucoside, the above described amounts of the botanical extract will be reduced by one-half.

In certain embodiments, the botanical extract forms approximately 50-70% w/w of the composition and the carrier or excipient forms approximately 50-30% w/w of the composition.

The botanical extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium* useful in the composition of the present invention is standardized with respect to luteolin-7 glucoside. In some embodiments, it is standardized to about 0.5-50% luteolin-7 glucoside; alternatively, about 1.0-30%; alternatively, about 0.5-5%; or about 1.0% luteolin-7 glucoside. One of skill in the art will appreciate that the extract may be standardized to other levels of luteolin-7 glucoside. For example, the botanical extract could be standardized to about 0.5%, 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10%, 15%, 20%, 25%, 30%, 35%, 40%, 45%, 50%, 55%, 60%, 65%, 70%, 75%, 80%, 85%, 90%, or 95% luteolin-7 glucoside content.

The compositions may have a pH between about 6.0 to about 8.0, or alternatively the composition may have a pH that is substantially neutral. In certain embodiments, the compositions in which the botanical extract is used have a generally neutral pH.

Certain embodiments relate to a composition for increasing skin whitening or lightening. The composition includes an effective amount of a botanical extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium* to reduce melanin production. The botanical extract may be standardized with respect to luteolin-7 glucoside. In some embodiments, it is standardized to about 0.5-50% luteolin-7 glucoside, alternatively, about 1.0-30%, or about 1.0% luteolin-7 glucoside. The composition may include a cosmetically acceptable vehicle.

Certain other embodiments relate to a composition for increasing skin whitening or lightening including a botanical extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium*, wherein the composition increases the whiteness or lightness of skin and such that the botanical extract is standardized with respect to 1.0% luteolin-7 glucoside. In some embodiments, it is standardized to about 5-50% luteolin-7 glucoside, alternatively, about 10-30%, or about 20% luteolin-7 glucoside.

Certain other embodiments relate to a composition for increasing skin whitening or lightening that includes a botanical extract of *Aspalathus Linearis, Matricaria, Saxifraga, Astragalus, Taraxacum officinale/mongolicum,*

*Ferula varia/foetida, Carthamus tinctorius, Sophora flavescentis,* or *Chrysanthemum morifolium,* wherein the compositions increases the whiteness or lightness of skin and such that the botanical extract is present in an amount from about 0.001% to about 10%.

Certain further embodiments relate to a method of increasing or skin whitening or lightening that includes administering to the subject a composition that includes a botanical extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium,* wherein the composition reduces or decreases melanogenesis, pigmentation, or both.

The compositions of the present invention may be prepared in various forms.

In certain embodiments, the compositions of the present invention may be prepared in forms suitable for intravenous, intraarterial, oral, parenteral, buccal, topical, transdermal, rectal, intramuscular, subcutaneous, intraosseous, transmucosal, or intraperitoneal routes of administration.

In certain embodiments, the compositions of the invention may be administered topically. For example, the topical compositions of the present invention may be in the form of a cosmetic preparation such as cream, cosmetic lotion, pack or powder, or as an emulsion, lotion, liniment foam, tablets, plasters, granules, aerosol spray, gel, mousse, pomade, or ointment. In each formulation, various known conventional cosmetic ingredients may be incorporated. For example, cosmetic ingredients such as alcohols, fats and oils, surfactants, fatty acids, silicone oils, humectants, moisturizers, viscosity modifiers, emulsifiers, stabilizers, coloring agents, and perfumes may be included. Certain further embodiments relate to compositions that may be formulated in any convenient form suitable for topical application to the skin. Suitable emulsions include oil-in-water, water-in-oil, and water-in-silicone emulsions.

In general, the compositions include a cosmetically acceptable vehicle. Examples of cosmetically acceptable vehicles suitable for all embodiments of the present invention include, but are not limited to, water, glycerin, various alcohols such as ethanol, propyl alcohol, vegetable oil, mineral oil, silicone oils, fatty ethers, fatty esters, fatty alcohols, glycols, polyglycols or any combinations thereof. Methods of formulation are well known in the art and are disclosed, for example, in Remington's Pharmaceutical Sciences, Gennaro, Mack Publishing Co., Easton Pa., 1990, which is incorporated herein by reference.

Alternatively, certain further embodiments relate to compositions that may be formulated in any convenient form suitable for oral administration; i.e., can be formed into any suitable, ingestible form. Suitable forms include capsules, tablets or caplets, capsules, lozenge, dragées or a plurality of particles, granules, beads, powders or pellets that may or may not be encapsulated. Other suitable forms include liquids, gels, syrups, slurries, suspensions, and other drink or food forms (chewable tablets, nutritional bars, soft gels, semi-solid taffy-like chews, and chewing gum) or the like. Soft chew is intended to mean a product which is solid at room temperature and which are soft to chew and which is functionally chewy because the product has some plastic texture during the process of mastication in the mouth. The dosage form is not limited with respect to size, shape or general configuration. The form may be configured as a single dosage form intended to provide a specified dose of the plant extract. For example, the single dosage form may be a pill, a tablet, a capsule, or a drink shot. The single dosage form may include from about 50 mg to about 2 g of the plant extract.

In certain embodiments, the compositions may further include one or more whitening agents to enhance the whitening effect of the composition. Exemplary whitening agents are believed to include all the known whitening agents and those that may be developed in the future. Preferably, the whitening agents are selected from the group consisting of tyrosinase inhibitors, free radical scavengers, and mixtures thereof. Examples of suitable tyrosinase inhibitors include, but are not limited to, kojic acid and its derivatives, arbutin and its derivatives, licorice extract and its derivatives, ascorbic acid and its derivatives, and hydroquinone and its derivatives. Examples of suitable free radical scavengers include, but are not limited to, licorice extract and its derivatives, vitamin E and its derivatives, vitamin A and its derivatives, vitamin C and its derivatives, Rosemary extract and its derivatives and superoxide dismutase. Preferred whitening agents are selected from the group consisting of kojic acid, derivatives of kojic acid, arbutin, derivatives of arbutin, bearberry extract, lemon extract, cucumber extract, vitamin C and its derivatives, extracts of acerola cherry and fermentates of acerola cherry.

Non-exclusive examples of the vitamin C derivatives are, for instance, alkyl esters of L-ascorbic acid such as L-ascorbyl palmitate, L-ascorbyl isopalmitate, L-ascorbyl dipalmitate, L-ascorbyl isostearate, L-ascorbyl distearate, L-ascorbyl diisostearate, L-ascorbyl myristate, L-ascorbyl isomyristate, L-ascorbyl 2-ethylhexanoate, L-ascorbyl di-2-ethylhexanoate, L-ascorbyl oleate and L-ascorbyl dioleate; phosphates of L-ascorbic acid such as L-ascorbyl-2-phosphate and L-ascorbyl-3-phosphate; sulfates of L-ascorbic acid such as L-ascorbyl-2-sulfate and L-acorbyl-3-sulfate; their salts with alkaline earth metals such as calcium and magnesium. They can be used alone or in a mixture of two or more.

When the botanical extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium* is mixed with any of the known whitening agents, the ratio of the botanical extract to the known whitening agent is from about 1:100 to about 100:1, preferably from about 1:50 to about 50:1, more preferably from about 1:10 to about 10:1. Most preferably, the ratio of botanical extract to known whitening agent is from about 1:5 to about 5:1.

In certain embodiments there is provided an improved skin whitening composition of the type containing skin whitening agents wherein the improvement comprises adding a botanical extract, such as at least one of Yarrow Extract (*Achillea millefolium*), *Aspalathus Linearis* Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*). The botanical extract may be standardized to about 0.5-50% luteolin-7 glucoside; alternatively, about 0.5-5%; or alternatively, about 1%. The composition may include a cosmetically acceptable vehicle. The composition may have a pH between about 6.0 to about 8.0, or alternatively the composition may have a pH that is substantially neutral.

Certain embodiment relates to a composition having a melanin synthesis-inhibiting activity, comprising an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* and *Chrysanthemum morifolium,* the botanical extract effective to reduce melanin synthesis. The composition has a substantially neutral pH. The botanical extract comprises at least one of Yarrow Extract, *Aspalathus Linearis* Extract, Chamomile Extract, *Saxifraga* Extract, Chinese Milk Vetch Extract, Dandelion Extract, *Ferula* Extract, Safflower Extract, Light Yellow *Sophora* Extract, and *Chrysanthemum* Extract. The botanical extract is standardized with respect to luteolin-7 glucoside content; wherein the botanical extract is standardized to about 0.5-50% luteolin-7 glucoside; or wherein the botanical extract is standardized to about 1% luteolin-7 glucoside. The amount effective to reduce melanin synthesis is from about 10 mg to about 1000 mg. The composition is formulated for an oral administration, the composition being a preparation selected from the group consisting of a capsule, a tablet, a chewable tablet, a caplet, a lozenge, a dragée, a plurality of particles, granules, beads, powders, pellets, a liquid, a gel, a syrup, a slurry, a suspension, a nutritional bar, a soft gel, a semi-solid taffy-like chew, and a chewing gum. The composition may further comprise a skin whitening agent selected from the group consisting of tyrosinase inhibitors, free radical scavengers, and mixtures thereof. The ratio of the botanical extract to the skin whitening agent may be from about 100:1 to about 1:100. The botanical extract forms approximately 1-99% w/w of the composition; the botanical extract forms approximately 1-75% w/w of the composition; or the botanical extract forms approximately 50-70% w/w of the composition. The botanical extract may be an aqueous extract of *Aspalathus Linearis, Matricaria, Saxifraga, Astragalus, Taraxacum officinale/mongolicum, Ferula varia/foetida, Carthamus tinctorius, Sophora flavescentis,* or *Chrysanthemum morifolium.* The composition may be for use in treating or preventing cholasma.

Another embodiment relates to an oral composition comprising a pharmaceutically acceptable vehicle and an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis,* and *Chrysanthemum morifolium* standardized to about 1.0% luteolin-7 glucoside, wherein the botanical extract forms approximately 1-99% w/w of the composition.

The compositions may be administered as needed, daily, several times per day or in any suitable regimen such that the desired outcome is achieved. The compositions may be administered on a continuous basis or intermittent basis.

Methods

The compositions described herein may be used for various cosmetic and/or pharmaceutical applications including inhibiting or reducing melanogenesis, mitigating or preventing cholasma or hyperpigmentation, and/or skin whitening and lightening.

Certain embodiments relate to a method of whitening skin that includes topically applying to the skin any composition described above and any combinations thereof.

Certain embodiments relate to a method of whitening skin that includes orally administering to a subject any composition described above and any combinations thereof.

Certain specific embodiments relate to a method of whitening skin that includes orally administering and/or topically applying to the skin a composition that includes an amount of a botanical extract (such as at least one of Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*), or a combination thereof) effective to reduce melanin synthesis, wherein the composition has a substantially neutral pH and wherein the composition is administered or applied in an amount and for a period of time sufficient to visibly whiten the skin. The botanical extract is standardized with respect to luteolin-7 glucoside. In some embodiments, it is standardized to about 0.5-50% luteolin-7 glucoside, preferably about 1-30%, or about 1% luteolin-7 glucoside. The botanical extract is present in an amount from about 0.001% to about 10%.

Certain other embodiments relate to a method of visibly whitening human skin comprising orally administering and/or topically applying to the skin a botanical extract (such as at least one of Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*)) standardized with respect to luteolin-7 glucoside in an amount and for a period of time sufficient to visibly whiten the skin. In some embodiments, it is standardized to about 0.5-50% luteolin-7 glucoside, alternatively, about 1-30%, or about 1% luteolin-7 glucoside.

Certain other embodiments relate to a method for inhibiting melanin synthesis comprising orally administering and/or topically applying to the skin a composition comprising an amount of a botanical extract (at least one of Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*)) standardized with respect toluteolin-7 glucoside and effective to reduce melanin synthesis, wherein the composition is administered and/or applied in an amount and for a period of time sufficient to inhibit melanin synthesis in the skin. In some embodiments, it is standardized to about 0.5-50% luteolin-7 glucoside, alternatively, about 1-30%, or about 1% luteolin-7 glucoside.

Certain other embodiments relate to a method for treating or preventing cholasma in a subject comprising orally administering and/or topically applying to the skin of the subject a composition comprising an amount of a botanical extract (an extract of at least one of Yarrow Extract (*Achillea millefolium*), *Aspalathus Linearis* Extract (Roobios; *Aspalathus Linearis*), Chamomile Extract (*Matricaria*), *Saxifraga* Extract (*Saxifraga*), Chinese Milk Vetch Extract (*Astragalus*), Dandelion Extract (Pu gong yin; *Taraxacum officinale/mongolicum*), *Ferula* Extract (*Ferula varia/foetida*), Safflower Extract (*Carthamus tinctorius*), Light Yellow *Sophora* Extract (*Sophora flavescentis*), or *Chrysanthemum* Extract (*Chrysanthemum morifolium*)) standardized with respect to luteolin-7 glucoside and effective to treat or prevent cholasma. In some embodiments, it is standardized to about 0.5-50% luteolin-7 glucoside, alternatively, about 1-30%, or about 1% luteolin-7 glucoside. The composition may have a substantially neutral pH and may be administered and/or applied in an amount and for a period of time sufficient to treat or prevent cholasma in the subject.

In a topical skin whitening cosmetic composition containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, the improvement comprising an effective amount of a botanical extract, such as an extract of at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*) to whiten the skin.

In the method, the frequency of oral and/or topical administrations will depend on several factors, including the desired level of suppression of melanogenesis. A suitable exemplary topical regimen includes application to the skin twice daily, with one application in the morning and one in the evening. A suitable exemplary oral regimen includes oral administration twice daily, with one administration in the morning and one in the evening. The amount of the composition used in each application or administration will also depend on several factors, including the desired level of suppression of melanogenesis and the content of the extract in the composition.

Certain specific embodiments relate to a method of whitening skin that includes topically applying to the skin a composition that includes an amount of a botanical extract (such as at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*), or a combination thereof) effective to reduce melanin synthesis, wherein the composition has a substantially neutral pH and wherein the composition is applied in an amount and for a period of time sufficient to visibly whiten the skin. The botanical extract is standardized with respect to luteolin-7 glucoside. In some embodiments, it is standardized to about 0.5-50% luteolin-7 glucoside, preferably about 1-30%, or about 1% luteolin-7 glucoside. The botanical extract is present in an amount from about 0.001% to about 10%.

Certain other embodiments relate to a method of visibly whitening human skin comprising topically applying to the skin a botanical extract (such as at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*)) standardized with respect to luteolin-7 glucoside in an amount and for a period of time sufficient to visibly whiten the skin. In some embodiments, it is standardized to about 0.5-50% luteolin-7 glucoside, alternatively, about 1-30%, or about 1% luteolin-7 glucoside.

Certain other embodiments relate to a method for inhibiting melanin synthesis comprising topically applying to the skin a composition comprising an amount of a botanical extract (at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*)) standardized with respect toluteolin-7 glucoside and effective to reduce melanin synthesis, wherein the composition is applied in an amount and for a period of time sufficient to inhibit melanin synthesis in the skin. In some embodiments, it is standardized to about 0.5-50% luteolin-7 glucoside, alternatively, about 1-30%, or about 1% luteolin-7 glucoside.

Certain other embodiments relate to a method for treating or preventing cholasma in a subject comprising topically applying to the skin of the subject a composition comprising an amount of a botanical extract (an extract of at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*)) standardized with respect to luteolin-7 glucoside and effective to treat or prevent cholasma. In some embodiments, it is standardized to about 0.5-50% luteolin-7 glucoside, alternatively, about 1-30%, or about 1% luteolin-7 glucoside. The composition may have a substantially neutral pH and may be applied in an amount and for a period of time sufficient to treat or prevent cholasma in the subject.

In a topical skin whitening cosmetic composition containing one or more cosmetic ingredients selected from the group consisting of alcohols, fats, oils, surfactants, fatty acids, silicone oils, humectants, moisturizers, viscosity modifiers, emulsifiers, stabilizers, coloring agents, and perfumes, the improvement comprising an effective amount of a botanical extract, such as an extract of at least one of Yarrow Extract (*Achillea millefolium*), Aspalathus Linearis Extract (Roobios; *Aspalathus Linearis*), Chamomile Extract (*Matricaria*), Saxifraga Extract (*Saxifraga*), Chinese Milk Vetch Extract (*Astragalus*), Dandelion Extract (Pu gong yin; *Taraxacum officinale/mongolicum*), Ferula Extract (*Ferula varia/foetida*), Safflower Extract (*Carthamus tinctorius*), Light Yellow Sophora Extract (*Sophora flavescentis*), or Chrysanthemum Extract (*Chrysanthemum morifolium*) to whiten the skin.

In the method, the frequency of topical applications will depend on several factors, including the desired level of suppression of melanogenesis. A suitable exemplary regimen includes application to the skin twice daily, with one application in the morning and one in the evening. The amount of the composition used in each application will also depend on several factors, including the desired level of suppression of melanogenesis and the content of the extract in the composition.

Another embodiment relates to a method of whitening skin comprising orally administering to a subject a composition comprising an amount of a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium*, wherein the composition is administered in an amount and for a period of time sufficient to visibly whiten the skin of the subject. The botanical extract is standardized to about 0.5-50% luteolin-7 glucoside.

Certain further embodiments relate to a method of visibly whitening human skin in a subject comprising orally administering to the subject a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized with respect to luteolin-7 glucoside in an amount sufficient to visibly whiten the skin.

Certain further embodiments relate to a method for inhibiting melanin synthesis comprising orally administering to a subject a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to reduce melanin synthesis, wherein the composition is administered in an amount and for a period of time sufficient to inhibit melanin synthesis in the skin.

Certain further embodiments relate to a method for treating or preventing cholasma comprising orally administering to a subject a composition comprising a botanical extract of at least one of *Aspalathus Linearis, Matricaria, Saxifraga, Astragalus, Taraxacum officinale/mongolicum, Ferula varia/foetida, Carthamus tinctorius, Sophora flavescentis*, and *Chrysanthemum morifolium* standardized to about 0.5-50% luteolin-7 glucoside and effective to treat or prevent cholasma, wherein the composition is administered in an amount and for a period of time sufficient to treat or prevent cholasma in the skin of the subject.

EXAMPLES

Example 1: Identification of Luteolin-7 Glucoside as an "Active" Marker for Skin Lightening Activity To determine the active component of the *chrysanthemum* extract, the following assay was performed.

Materials and Instrumentation:

All solvents were HPLC grade and purchased from Fisher Scientific. HPLC separation was achieved using an Agilent Technologies HP1100 System equipped with Photodiode-array detection and Chemstation software. The column was from Agilent, Zorbax SB-C18 5u 4.6×250 mm Cat. No: 880975-902

Standard Compound:

Luteolin-7-O-Glucoside, Chromadex Cat. No. ASB-00012500-010 (CAS #:5371-11-5)

Sample Preparation:

Approximately 400 mg of dry powdered sample of *Chrysanthemum* was weighted, to the nearest 0.1 mg, into a 50 mL volumetric flask. About 40 mL of 80/20 Methanol was added in DI Water (diluent) and shaken well to dissolve. The solution was placed in a sonic bath and sonicated for 10 minutes, then cooled to room temperature, diluted to volume with diluent and mixed thoroughly. The sample solution was then filtered with a disposable syringe through a 0.45 micron PVDF filter into an HPLC auto sampler vial.

HPLC Conditions:

| Gradient Mobile Phase: | | |
|---|---|---|
| Time | A: 0.2% o-Phosphoric acid in HPLC Grade water | B: ACN (Acetonitrile) |
| 0.0 | 84 | 16 |
| 5.0 | 80.5 | 19.5 |
| 30.0 | 59.5 | 40.5 |
| 35.0 | 50 | 50 |
| 35.1 | 84 | 16 |
| 38.0 | 84 | 16 |

| | |
|---|---|
| Flow Rate: | 1.0 mL/min |
| Column Temperature: | Ambient |
| Injection Volume: | 10 μL |
| Detection Wavelength: | 370 nm |
| Integration: | Peak area |
| Run Time: | 38 minutes |

Figure 1:
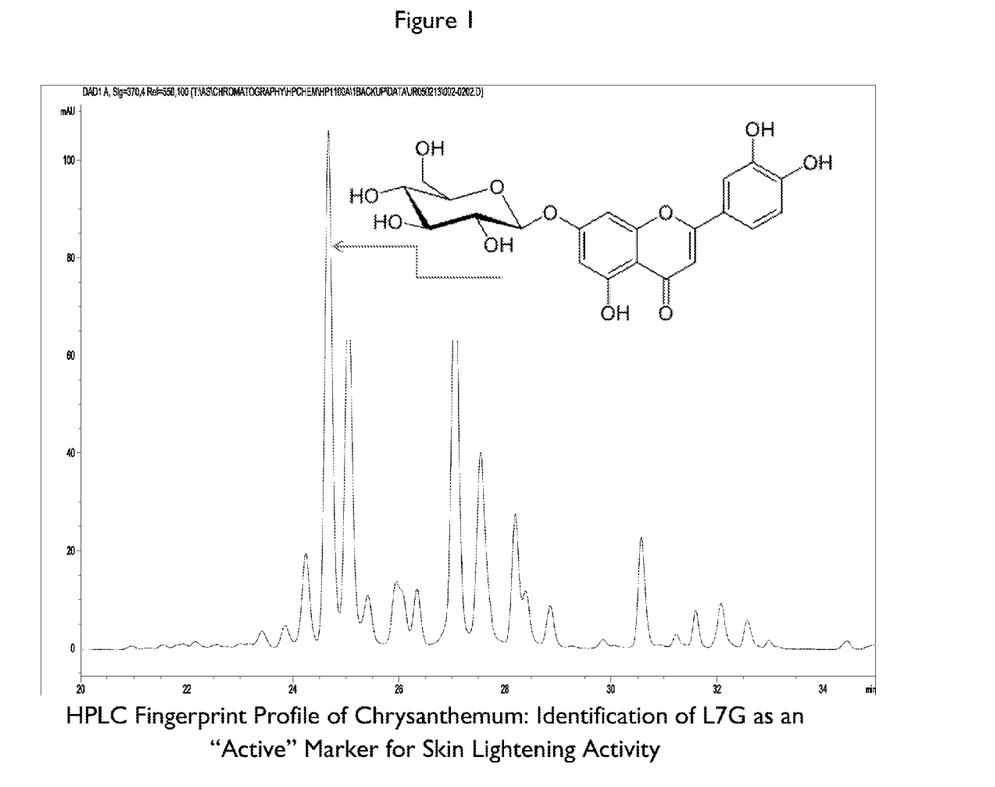
FIG. 1 depicts an HPLC fingerprint profile of *chrysanthemum*.

FIG. 1 shows the HPLC fingerprint profile of *chrysanthemum*. Luteolin-7 glucoside was identified as the active marker for skin lightening activity.

Example 1: Dose-Dependent Inhibition of Tyrosinase Enzyme Activity by *Chrysanthemum* Extract To determine if *chrysanthemum* extract affected tyrosinase enzyme activity, the following assay was performed.

Tyrosinase inhibition assay was performed using enzyme extracted and partially purified from B16 melanoma cells. B16 tyrosinase enzyme partially purified using one step DEAE ion exchange column was used as the enzyme source. Reaction mixture containing 20 μl of L-dopa (10 mM) and 20 μl of tyrosinase enzyme (specific activity: 200 nmoles/mg protein) and 160 μl of the 50 mM Phosphate buffer (pH6.8) (with or without *chrysanthemum* extract) was added to a 96-well microplate. Final concentration of L-dopa was maintained at 1 mM. The enzyme activity was measured kinetically at 1 minute intervals for 30 minutes at 37° C. for the formation of dopachrome at 475 nm using an M5 microplate reader (Molecular Devices). The percent inhibition of tyrosinase activity was calculated as follows:

$$\% \text{ Inhibition} = [(A-B)/A] * 100$$

Where A is the difference in absorption of the control sample between the samples with and without tyrosinase and B is the difference in absorption of the test sample between the sample with and without tyrosinase (Diwakar G, Rana J, Scholten J D. Inhibition of melanin production by a combination of Siberian larch and pomegranate fruit extracts. Fitoterapia, 2012; 83:989-95).

Figure 2:
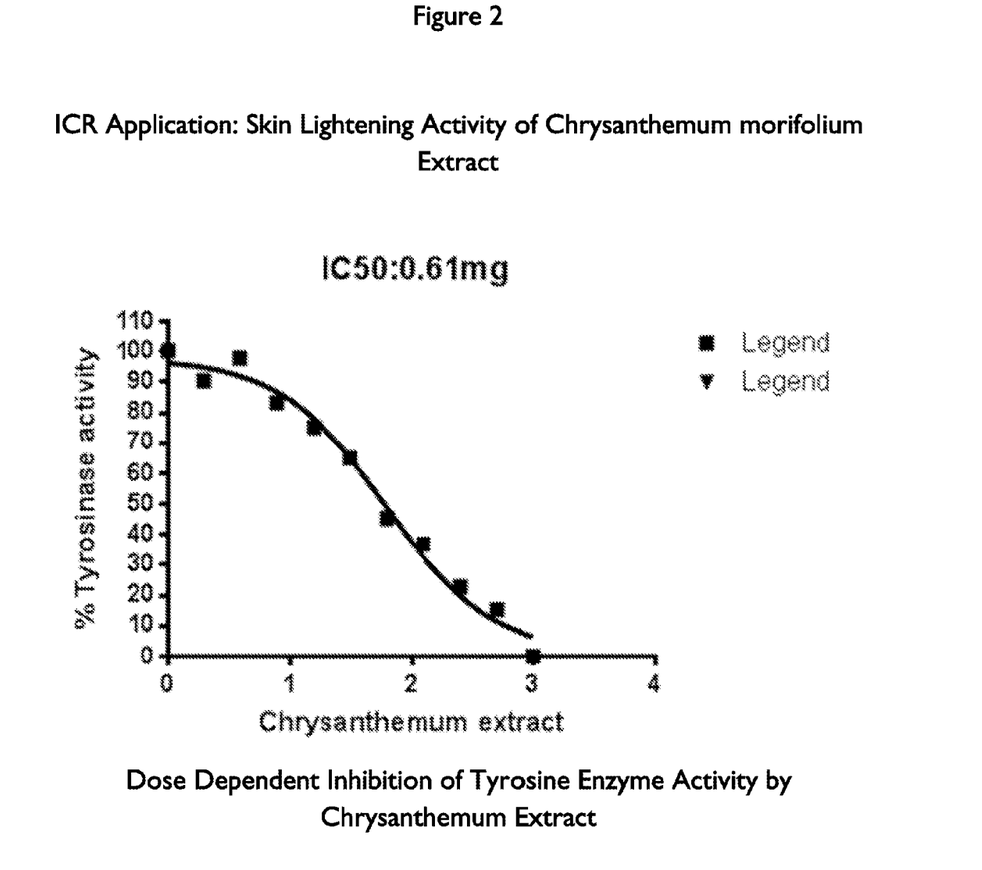
FIG. 2 depicts a graph showing a dose-dependent inhibition of tyrosinase enzyme activity by *chrysanthemum* extract.

As shown in FIG. 2, administration of *chrysanthemum* extract resulted in a dose-dependent inhibition of tyrosinase enzyme activity by *chrysanthemum* extract.

Example 2: *Chrysanthemum* Extract Standardized to about 1.0% Luteolin-7 Glucoside Demonstrated Dose Dependent Reduction of Melanin Production To determine if the luteolin-7 glucoside present in *chrysanthemum* affected melanin production, the following assay was performed.

Standardized *chrysanthemum* extract containing 20% luteolin-7 glucoside was tested.

The *chrysanthemum* extract in an amount of 25 μg and 12.5 μg was solubilized in DMSO and added to Melan-a cells that were freshly seeded at a density of $5 \times 10^4$ cells on a 24 well plate. The cytosolic pH of the Melan-a melanocytes in this assay is about 5-7. Each dose of the *chrysanthemum* extract was added to the cells in triplicate. The final concentration of DMSO in the culture medium was maintained at 0.25%. Forty eight hours following the first set of treatment, the cells were again treated with the *chrysanthemum* extract and supplemented with fresh medium. Two days later, melanin was extracted and quantified by normalizing with protein content, following the method described by Komatsu et al. (*J. Cosmet. Sci;* 64, 455-453 (2013); Rana J. et al., *Pigment Cell Res.*, 18:447 (2005)).

Inhibitory activity of samples was reported as % reduction in melanin production compared to 100% untreated control (UT). Phenylthiourea (PTU), a well-known tyrosinase inhibitor was used as positive inhibitor control in the assay. FIG. 3 plots the results. It can be seen that the use of a *chrysanthemum* extract standardized to 20% luteolin-7 glucoside provided a dose dependent reduction in melanin production.

It is therefore intended that the foregoing detailed description be regarded as illustrative rather than limiting, and that it be understood that it is the following claims, including all equivalents, that are intended to define the spirit and scope of this invention.

The invention claimed is:

1. A method of whitening skin comprising topically applying to the skin a composition comprising at least 50% w/w of a botanical extract of at least one of *Aspalathus Linearis, Matricaria, Saxifraga, Astragalus, Taraxacum officinale/mongolicum, Ferula varia/foetida, Carthamus tinctorius, Sophora flavescens*, and *Chrysanthemum morifolium* standardized to about 0.5-50% luteolin-7 glucoside, wherein the composition is applied in an amount and for a period of time sufficient to visibly whiten the skin.

2. The method of claim 1, wherein the botanical extract is standardized to about 1% luteolin-7 glucoside.

3. A method of visibly whitening human skin comprising topically applying to the skin an effective amount of botanical extract of at least one of *Aspalathus Linearis, Matricaria, Saxifraga, Astragalus, Taraxacum officinale/mongolicum, Ferula varia/foetida, Carthamus tinctorius, Sophora flavescens*, and *Chrysanthemum morifolium*, standardized to about 0.5-50% luteolin-7 glucoside in an amount and for a period of time sufficient to visibly whiten the skin.

4. The method of claim 3, wherein the botanical extract is standardized to about 1% luteolin-7 glucoside.

5. The method of claim 3, wherein the botanical extract is incorporated into a cosmetic preparation selected from the group consisting of cream, ointment, foam, lotion, plaster, tablets, granules, and emulsion.

6. The method of claim 5, wherein the cosmetic preparation further comprises a skin whitening agent selected from the group consisting of tyrosinase inhibitors, free radical scavengers, and mixtures thereof.

7. The method of claim 6, wherein the ratio of the botanical extract to the skin whitening agent is from about 100:1 to about 1:100.

8. A method for inhibiting melanin synthesis comprising topically applying to the skin a composition comprising at least 50% w/w of a botanical extract of at least one of *Aspalathus Linearis, Matricaria, Saxifraga, Astragalus, Taraxacum officinale/mongolicum, Ferula varia/foetida, Carthamus tinctorius, Sophora flavescens*, and *Chrysanthemum morifolium* standardized to about 0.5-50% luteolin-7 glucoside and effective to reduce melanin synthesis, wherein the composition is applied in an amount and for a period of time sufficient to inhibit melanin synthesis in the skin.

9. A method for treating or preventing cholasma comprising topically applying to the skin of a subject a composition comprising at least 50% w/w of a botanical extract of at least one of *Aspalathus Linearis, Matricaria, Saxifraga, Astragalus, Taraxacum officinale/mongolicum, Ferula varia/foetida, Carthamus tinctorius, Sophora flavescens*, and *Chrysanthemum morifolium* standardized to about 0.5-50% luteolin-7 glucoside and effective to treat or prevent cholasma, wherein the composition is applied in an amount and for a period of time sufficient to treat or prevent cholasma in the skin of the subject.

* * * * *